(12) United States Patent
Roettger et al.

(10) Patent No.: US 11,746,075 B2
(45) Date of Patent: Sep. 5, 2023

(54) METHOD FOR THE SIMULTANEOUS PRODUCTION OF SODIUM AND POTASSIUM ALCOHOLATES

(71) Applicant: Evonik Functional Solutions GmbH, Niederkassel (DE)

(72) Inventors: Dirk Roettger, Cologne (DE); Sebastian Reimann, Wesseling (DE); Manfred Neumann, Marl (DE); Moritz Schröder, Muenster (DE); Philip Zitzewitz, Haltern am See (DE); Niklas Paul, Marl (DE); Armin Matthias Rix, Marl (DE)

(73) Assignee: Evonik Functional Solutions GmbH, Niederkassel (DE)

( * ) Notice: Subject to any disclaimer, the term of this patent is extended or adjusted under 35 U.S.C. 154(b) by 0 days.

(21) Appl. No.: 17/759,143

(22) PCT Filed: Nov. 30, 2020

(86) PCT No.: PCT/EP2020/083877
§ 371 (c)(1),
(2) Date: Jul. 20, 2022

(87) PCT Pub. No.: WO2021/148174
PCT Pub. Date: Jul. 29, 2021

(65) Prior Publication Data
US 2023/0028559 A1 Jan. 26, 2023

(30) Foreign Application Priority Data
Jan. 23, 2020 (EP) .................................. 20153334

(51) Int. Cl.
*C07C 29/70* (2006.01)
*C07C 29/80* (2006.01)

(52) U.S. Cl.
CPC ............ *C07C 29/705* (2013.01); *C07C 29/80* (2013.01)

(58) Field of Classification Search
CPC ............................. C07C 29/705; C07C 29/80
See application file for complete search history.

(56) References Cited

U.S. PATENT DOCUMENTS 1,910,331 A 5/1933 Halbig
2,295,256 A 9/1942 Brugma
(Continued)

FOREIGN PATENT DOCUMENTS

CN 208632416 U 3/2019
DE 968 903 C 4/1958
(Continued)

OTHER PUBLICATIONS

Dejanovié et al., "Dividing wall column—A breakthrough towards sustainable distilling", Chemical Engineering and Processing: Process Intensification, vol. 49, 2010, pp. 559-580.
(Continued)

*Primary Examiner* — Deborah D Carr
(74) *Attorney, Agent, or Firm* — Grüneberg and Myers PLLC (57) ABSTRACT

A process can be used for preparing sodium and potassium alkoxides. The process is characterized by two simultaneously implemented but spatially separated reactions of an alcohol ROH with NaOH, and ROH with KOH, to give sodium alkoxide and potassium alkoxide, respectively. The vapours formed in this case contain the alcohol used and water. The vapours are combined, and the resulting mixed vapour is fed to a common distillation with recovery of the alcohol.

16 Claims, 5 Drawing Sheets

(56) References Cited

U.S. PATENT DOCUMENTS

| | | |
|---|---|---|
| 2,877,274 A | 3/1959 | Kramis |
| 4,566,947 A | 1/1986 | Tsuruta |
| 4,895,989 A | 1/1990 | Sander et al. |
| 7,273,956 B2 | 9/2007 | Ruwwe et al. |
| 7,847,133 B2 | 12/2010 | Ruwwe et al. |
| 2002/0183566 A1 | 12/2002 | Guth et al. |
| 2004/0097759 A1 | 5/2004 | Ruwwe et al. |
| 2008/0296786 A1 | 12/2008 | Ruwwe et al. |
| 2011/0313207 A1 | 12/2011 | Kaibel et al. |
| 2013/0023683 A1 | 1/2013 | Ruwwe et al. |

FOREIGN PATENT DOCUMENTS

| | | |
|---|---|---|
| EP | 0 122 367 | 10/1984 |
| EP | 0 126 288 | 11/1984 |
| EP | 3 184 502 | 6/2017 |
| GB | 377 631 | 7/1932 |
| GB | 737 453 | 9/1955 |
| WO | 2021/148174 | 7/2021 |
| WO | 2021/148175 | 7/2021 |

OTHER PUBLICATIONS

Hossain et al., "Effects of catalyst types and concentrations on biodiesel production from waste soybean oil biomass as renewable energy and environmental recycling process", Australian Journal of Crop Science, vol. 4, No. 7, 2010, pp. 550-555.

International Search Report dated Feb. 26, 2021 in PCT/EP2020/083877, with English translation, 5 pages.

Written Opinion dated Feb. 26, 2021 in PCT/EP2020/083877, with English translation, 8 pages.

U.S. Appl. No. 60/935,715, filed Aug. 28, 2007, Ruwwe et al.

U.S. Appl. No. 13/552,707, filed Jul. 19, 2012, 2013/0023683, Ruwwe et al.

U.S. Appl. No. 17/659,086, filed Apr. 13, 2022, Roettger et al.

METHOD FOR THE SIMULTANEOUS PRODUCTION OF SODIUM AND POTASSIUM ALCOHOLATES

CROSS-REFERENCE TO RELATED APPLICATIONS

This application is the National Stage entry under § 371 of International Application No. PCT/EP2020/083877, filed on Nov. 30, 2020, and which claims the benefit of priority to European Application No. 20153334.6, filed on Jan. 23, 2020. The content of each of these applications is hereby incorporated by reference in its entirety.

BACKGROUND OF THE INVENTION

Field of the Invention

The present invention relates to a process for preparing sodium and potassium alkoxides. It is characterized by two simultaneously implemented but spatially separated reactions of an alcohol ROH with NaOH and KOH to give sodium alkoxide and potassium alkoxide respectively. The vapours formed in this case comprise the alcohol used and water. They are combined and the resulting mixed vapour fed to a common distillation with recovery of the alcohol.

Description of Related Art

Alkali metal alkoxides are used as strong bases in the synthesis of numerous chemicals, for example in the production of pharmaceutical or agrochemical active ingredients. Furthermore, alkali metal alkoxides are used as catalysts in transesterification and amidation reactions.

Alkali metal alkoxides (MOR) are prepared by means of reactive distillation of alkali metal hydroxides (MOH) and alcohols (ROH) in a countercurrent distillation column, wherein the water of reaction formed according to the following reaction is removed with the distillate.

$$MOH + ROH \rightleftharpoons MOR + H_2O$$

Such a process principle is described, for example, in U.S. Pat. No. 2,877,274 A, wherein aqueous alkali metal hydroxide solution and gaseous methanol are driven in countercurrent into a rectification column. In principle, this process is described again in unchanged form in WO 01/42178 A1.

Similar processes, but in which in addition an entrainer such as benzene is also used, are described in GB 377,631 A and U.S. Pat. No. 1,910,331 A. The entrainer in this case serves the purpose of separating water and the water-soluble alcohol. In both patent documents, the condensate is subjected to a phase separation in order to separate off the water of reaction.

Accordingly, DE 96 89 03 C describes a process for the continuous production of alkali metal alkoxides in a reaction column, wherein the water-alcohol mixture removed at the head of the column is condensed and then subjected to a phase separation. The aqueous phase is discarded in this case and the alcoholic phase, together with fresh alcohol, is returned to the head of the column. EP 0 299 577 A2 describes a similar process, wherein the water in the condensate is separated off with the aid of a membrane.

The industrially important alkali metal alkoxides are those of sodium and potassium, and especially here the methoxides and ethoxides. Their synthesis is frequently described in the prior art, for example in EP 1 997 794 A1.

In some technical fields, for example in the production of biodiesel, there is a need for both alkoxides, those of potassium and also those of sodium (compare e.g. A.B.M.S. Hossain, M. A. Mazen, *Australian Journal of Crop Science* 2010, 4 (7), 550-555).

Therefore, there is a requirement for processes for the efficient production of alkoxides of both alkali metals.

Methods have been described in the prior art with which in principle alkoxides of both alkali metals, of sodium and of potassium, can be produced.

For instance, CN 208632416 U describes a process for the continuous production of solutions of sodium methoxide ("NM" in the following) and potassium methoxide ("KM" in the following) via reactive rectification. This process is characterized in that the process can be rapidly switched between the reaction to give NM or KM. However, in a certain period, only either NM or KM can be continuously produced. This is economically disadvantageous per se. In addition, in such a multi-purpose plant, product impurity and/or product loss occur on product changeover such that NM impurities arise in KM and vice versa. In order to minimize these, a laborious cleaning of the plant is required on each changeover of the alkali metal.

SUMMARY OF THE INVENTION

The object of the present invention therefore consisted of providing an improved process which allows efficient production of sodium and potassium alkoxides. Such a process should in particular eliminate the disadvantages of the processes described in the prior art, such as the cross-contamination of one alkali metal alkoxide with the other and product loss on changeover of the reactant.

A process which achieves the object according to the invention has now surprisingly been found.

The preferably continuous process according to the invention is one for producing sodium alkoxide of the formula RONa and potassium alkoxide of the formula ROK, wherein (a) ROH is reacted with NaOH in countercurrent, whereby RONa and a vapour $B_1$ comprising water and ROH are obtained, (b) ROH is reacted with KOH in countercurrent, whereby ROK and a vapour $B_2$ comprising water and ROH are obtained, wherein R is a $C_1$-$C_6$-hydrocarbon radical, characterized in that the reactions according to (a) and (b) proceed simultaneously and spatially separated, and that the vapours $B_1$ and $B_2$ are at least partially mixed to give mixed vapour $B_M$ comprising ROH and water, and that ROH is at least partially separated off from $B_M$ by distillation.

DETAILED DESCRIPTION OF THE INVENTION

The process according to the invention is characterized in that sodium alkoxide and potassium alkoxide are produced simultaneously and spatially separated and the respective resulting vapours comprising water and alcohol ROH are fed as a mixture to a distillation for separating off and especially recovery of the alcohol. This allows a particularly efficient production of the respective alkoxides since cleaning of the relevant reaction column is unnecessary and the impurities of both alkoxides RONa in ROK are avoided as a result. In addition, the process according to the invention offers the advantage, unlike in the processes of the prior art that must be switched back and forth between campaigns, that both alkoxides RONa and ROK can be produced simultaneously.

In step (a) and step (b) of the process according to the invention, the alcohol ROH is reacted in each case with NaOH or KOH in countercurrent, whereby the corresponding sodium alkoxide of the formula RONa and a vapour $B_1$ or the corresponding potassium alkoxide of the formula ROK and a vapour $B_2$ are obtained. The vapours $B_1$ and $B_2$ each comprise ROH and water. These are at least partially mixed to give the mixed vapour $B_M$ comprising ROH and water. From this, ROH is at least partially separated off by distillation.

In a preferred embodiment of the present invention, the alcohol ROH thus separated off from $B_M$ is used again in reaction (a) and/or reaction (b), preferably in both reactions (a) and (b).

In the process according to the invention, R is a $C_1$-$C_6$-hydrocarbon radical, preferably selected from the group consisting of methyl, ethyl, n-propyl, isopropyl, n-butyl, sec-butyl, isobutyl, tert-butyl, isomers of pentyl such as n-pentyl, more preferably selected from the group consisting of methyl, ethyl, n-propyl, isopropyl, even more preferably selected from the group consisting of methyl, ethyl. R is particularly preferably methyl and ROH is accordingly methanol.

In a preferred embodiment of the process according to the invention, NaOH is added to the reaction in step (a) and/or KOH in the reaction according to (b) in at least one solvent selected from water, ROH, preferably dissolved in a mixture of ROH and water.

This signifies that preferably in step (a) of the process according to the invention, NaOH is added in water, in ROH or in a water/ROH mixture, wherein addition in water or ROH is preferred and addition in water is particularly preferred.

This signifies that preferably in step (b) of the process according to the invention, KOH is added in water, in ROH or in a water/ROH mixture, wherein addition in water or ROH is preferred and addition in water is particularly preferred.

If NaOH is added in water in step (a) of the process according to the invention, the proportion by mass of NaOH, based on the total weight of the aqueous solution, is particularly in the range of 10 to 55% by weight, preferably 15 to 54% by weight, more preferably 30 to 53% by weight and particularly preferably 45 to 52% by weight. Most preferably, the proportion of NaOH in the aqueous solution is 50% by weight.

If KOH is added in water in step (b) of the process according to the invention, the proportion by mass of KOH, based on the total weight of the aqueous solution, is particularly in the range of 10 to 55% by weight, preferably 15 to 54% by weight, more preferably 30 to 53% by weight and particularly preferably 45 to 52% by weight. Most preferably, the proportion of KOH in the aqueous solution is 50% by weight.

The alcohol ROH used in the process according to the invention can serve both as solvent and as reactant. Furthermore, the alcohol ROH used can serve the purpose of stripping out water from the respective reaction mixture so that this can be removed via the distillate.

In a preferred embodiment of the process according to the invention, and particularly in the cases where NaOH is added in water in step (a), the ratio of total weight (mass; unit: kg) of alcohol ROH used in step (a) to the total weight (mass; unit: kg) of NaOH used in step (a) is from 4:1 to 50:1, more preferably from 9:1 to 48:1, yet more preferably from 13:1 to 35:1.

In this preferred embodiment of the process according to the invention, and particularly in the cases where KOH is added in water in step (b), the ratio of total weight (mass; unit: kg) of alcohol ROH used in step (b) to the total weight (mass; unit: kg) of KOH used in step (b) is from 4:1 to 50:1, more preferably from 9:1 to 48:1, yet more preferably from 13:1 to 35:1.

If NaOH or KOH are added in ROH or in a mixture of ROH and water in step (a) or (b) of the process according to the invention, the alcohol ROH is preferably the one intended to be reacted with NaOH and KOH in reaction (a) or (b).

If NaOH is added in ROH in step (a) of the process according to the invention, the proportion by mass of NaOH in ROH, based on the total weight of the solution, is particularly in the range of 10 to 55% by weight, preferably 15 to 54% by weight, more preferably 30 to 53% by weight and particularly preferably 45 to 52% by weight.

If KOH is added in ROH in step (b) of the process according to the invention, the proportion by mass of KOH in ROH, based on the total weight of the solution, is particularly in the range of 10 to 55% by weight, preferably 15 to 54% by weight, more preferably 30 to 53% by weight and particularly preferably 45 to 52% by weight.

If NaOH is added in a mixture of water and ROH in step (a) of the process according to the invention, the proportion by mass of NaOH in ROH and water, based on the total weight of the solution, is particularly in the range of 10 to 55% by weight, preferably 15 to 54% by weight, more preferably 30 to 53% by weight and particularly preferably 45 to 52% by weight.

If KOH is added in a mixture of water and ROH in step (b) of the process according to the invention, the proportion by mass of KOH in ROH and water, based on the total weight of the solution, is particularly in the range of 10 to 55% by weight, preferably 15 to 54% by weight, more preferably 30 to 53% by weight and particularly preferably 45 to 52% by weight.

The alcohol ROH used in step (a) and in step (b) of the process according to the invention in the inventive configuration of the process can also be commercial alcohol having a proportion by mass of alcohol of more than 99.8% by weight and a proportion by mass of water of up to 0.2% by weight.

The reactions in step (a) and step (b) of the process according to the invention are carried out particularly at a temperature in the range of 45'C to 150° C., preferably 47° C. to 120° C., more preferably 60° C. to 110° C., and at a pressure of 0.5 bar to 40 bar, preferably in the range of 0.75 bar to 5 bar, more preferably in the range of 1 bar to 2 bar, more preferably in the range of 1 bar to 1.5 bar, even more preferably at atmospheric pressure (1 bar).

The steps (a) and (b) of the process according to the invention are carried out spatially separated, wherein the vapours $B_1$ and $B_2$ are at least partially mixed to give mixed vapour $B_M$ comprising ROH and water, and ROH is at least partially separated off from $B_M$ by distillation.

The at least partial mixing of vapours $B_1$ and $B_2$ to give mixed vapour $B_M$ comprising ROH and water is not particularly restricted and is possible according to processes known to those skilled in the art. It suffices in particular to merge at least partially the vapours $B_1$ and $B_2$ to give the mixed vapour $B_M$. From this ROH is then separated off by processes known to those skilled in the art, for example in a rectification column.

The alcohol ROH separated off from $B_M$ is particularly used again in reaction (a) and/or reaction (b), preferably in reaction (a) and reaction (b).

It is critical that the process according to the invention is carried out spatially separated and simultaneously. Several embodiments are described below according to which this spatial separation with simultaneous reaction is preferably achieved.

In a first preferred embodiment, this spatially separated, simultaneous reaction is ensured by carrying out the reaction according to (a) in a first reaction column and the reaction according to (b) in a second reaction column different from the first.

In a second preferred embodiment, this spatially separated, simultaneous reaction is ensured by carrying out the reaction according to (a) and the reaction according to (b) in the same reaction column in which they are separated from each other by at least one dividing wall.

In a third preferred embodiment, this spatially separated, simultaneous reaction is ensured by carrying out the process according to the invention in a reaction column comprising a dividing wall and preferably a rectifying section, and a side column to the reaction column, wherein one of the two steps (a) and (b) is carried out in one of the regions of the reaction column segregated by the dividing wall, and the other of the two steps (a) and (b) is carried out in the side column, and the at least partial distillative separation of ROH from $B_M$ takes place in the region of the reaction column segregated by the dividing wall, in which neither of the steps (a), (b) is carried out, and preferably the rectifying section.

The RONa obtained in step (a) is preferably obtained as a solution $L_{NM}$ of RONa in ROH. Even more preferably, $L_{NM}$ then has a proportion by mass of RONa in ROH in the range 1 to 50% by weight, preferably 5 to 32% by weight, more preferably 15 to 32% by weight, most preferably 30 to 32% by weight, based in each case on the total solution $L_{NM}$. The proportion by mass of RONa in ROH can be adjusted in this case by means familiar to those skilled in the art, for example an additional evaporator at the bottom of a reaction column. The proportion by mass of residual water in $L_{NM}$ is preferably in this case <1% by weight, preferably <0.1% by weight, more preferably <0.01% by weight, based in each case on the total solution $L_{NM}$. The proportion by mass of NaOH in $L_{NM}$ is preferably in this case <1% by weight, preferably <0.1% by weight, more preferably <0.01% by weight, based in each case on the total solution $L_{NM}$.

The ROK obtained in step (b) is preferably obtained as a solution $L_{KM}$ of ROK in ROH. Even more preferably, $L_{KM}$ then has a proportion by mass of ROK in ROH in the range 1 to 50% by weight, preferably 5 to 32% by weight, more preferably 15 to 32% by weight, most preferably 30 to 32% by weight, based in each case on the total solution $L_{KM}$. The proportion by mass of ROK in ROH can be adjusted in this case by means familiar to those skilled in the art, for example an additional evaporator at the bottom of a reaction column. The proportion by mass of residual water in $L_{KM}$ is preferably in this case <1% by weight, preferably <0.1% by weight, more preferably <0.01% by weight, based in each case on the total solution $L_{KM}$. The proportion by mass of KOH in $L_{KM}$ is preferably in this case <1% by weight, preferably <0.1% by weight, more preferably <0.01% by weight, based in each case on the total solution $L_{KM}$.

1. First Preferred Embodiment: (a) and (b) Each in Different Reaction Columns

In a first preferred embodiment of the process according to the invention, the spatial separation of reactions (a) and (b) is achieved by carrying out the reaction according to (a) in a first reaction column and the reaction according to (b) in a second reaction column different from the first.

"Reaction column" or "RD" is used in accordance with the invention as abbreviation for "reactive rectification column", The reaction column preferably comprises internals. Suitable internals are, for example, trays, structured packings or unstructured packings. If the reaction column comprises trays, bubble cap trays, tunnel cap trays, Thormann trays, cross-slit bubble cap trays, valve trays or sieve trays are suitable. If the reaction column comprises trays, those trays are preferably selected in which at most 5%, preferably less than 1% of the liquid trickles through the relevant trays. The constructive measures required to minimize trickle-through of the liquid are familiar to those skilled in the art. In the case of valve trays, particularly tightly closing valve designs are selected for example. By reducing the number of valves, the vapour velocity in the tray openings can also be increased to double the value which is typically set. When using sieve trays, it is particularly favourable to reduce the diameter of the tray openings and to maintain or even increase the number of openings.

When using structured or unstructured packings, structured packings are preferred with regard to the uniform distribution of the liquid. In this embodiment, in all sections of the column cross-section which correspond to more than 2% of the total column cross-section, the average ratio of liquid stream to vapour stream, with respect to the liquid, also may be exceeded by not more than 15%, preferably by not more than 3%. This minimized liquid amount makes it possible for the capillary effect at the wire meshes to eliminate local peaks of liquid trickling density.

For columns comprising unstructured packings, especially comprising random packings, and for columns comprising structured packings, the desired characteristics of the liquid distribution may be achieved when the liquid trickling density in the edge region of the column cross-section adjacent to the column shell, corresponding to about 2% to 5% of the total column cross-section, is reduced compared to the other cross sectional regions by up to 100%, preferably by 5% to 15%. This is easily achievable for example through specific distribution of the drip points of the liquid distributors or their bores.

In the first preferred embodiment, KOH and NaOH are in particular each fed to the upper half, preferably to the upper third, more preferably to the upper quarter, of the respective reaction column. This is advantageous since it prevents contamination of the vapour by NaOH, KOH or alkoxide.

Of advantage in all preferred embodiments of the process according to the invention is to feed to the reaction column the NaOH or KOH solution heated, particularly at a temperature just below the boiling point, particularly 1 to 10° C. more preferably 1° to 5° C., most preferably 2 to 3° C. below the boiling point of the respective solution. When using an aqueous sodium hydroxide or potassium hydroxide solution, this is heated preferably to a temperature of 50 to 70° C., for example by means of a heat exchanger, prior to being fed to the relevant reaction column. The feed temperature of the alkali metal hydroxide solution preferably has the temperature of the tray at the feed point of the alkali metal hydroxide solution.

In all preferred embodiments of the process according to the invention, the alcohol ROH can be used either as a vapour or liquid, preferably as a vapour. The alcohol ROH is preferably fed to the bottom, into the evaporator (in the preferred cases in which the respective reaction column has one such), on a tray or onto two or more trays which are preferably located 1 to 10, particularly preferably 1 to 6 trays above the bottom. In particular, in the process according to the invention, the alcohol ROH is fed in gaseous form to the bottom or into the evaporator of the reaction column.

"Reaction in countercurrent" is ensured in particular in accordance with the invention in that the addition point to the respective column of at least part of the alcohol ROH used in step (a) is below the addition point of NaOH [in reaction (a)] or KOH [in reaction (b)]. This is applicable to all embodiments of the invention. The reaction column, in which the respective alkali metal alkoxide NaOR or KOR is produced, preferably comprises at least 2, particularly 15 to 40 theoretical trays between the feed point of NaOH or KOH and the addition point of the alcohol ROH.

Step (a) of the process according to the invention also comprises the case where a portion of the ROH is added in vaporous form below the feed point of the respective NaOH or KOH aqueous alkaline solution but nevertheless at the upper end or in the region of the upper end of the respective reaction column. This makes it possible to reduce the dimensions of the lower region of the respective reaction column. When a portion of the methanol is added in vaporous form at the upper end or in the region of the upper end of the reaction column, only a fraction of 10% to 70% by weight, preferably 30% to 50% by weight, [in each case based on the total amount of the alcohol used in step (a) or (b)] is fed to the lower end of the reaction column and the remaining fraction is added in vaporous form in a single stream or divided into a plurality of substreams, preferably 1 to 10 theoretical trays, particularly preferably 1 to 3 theoretical trays, below the respective feed point of NaOH or KOH. This is applicable to all preferred embodiments of the process according to the invention.

In the first preferred embodiment of the process according to the invention, a vapour is obtained in each case at the head of each reaction column: $B_1$, which is obtained at the head of the reaction column in which NaOH and ROH are reacted in countercurrent, comprises water and ROH. $B_2$, which is obtained at the head of the reaction column in which KOH and ROH are reacted in countercurrent, comprises water and ROH.

In the first preferred embodiment of the process according to the invention, both reaction columns may be operated with or without return flow. In a preferred embodiment, the first and/or the second, preferably both reaction columns different from each other, has a return flow. This means that $B_1$ and/or $B_2$ are at least partially, preferably partially, fed back again to the reaction column as return flow. In the cases where such a return flow is established, the return ratio is preferably at least 0.05 to 0.99, more preferably 0.1 to 0.9, yet more preferably 0.11 to 0.34, particularly preferably 0.14 to 0.27 and especially preferably 0.17 to 0.24. A return flow can be adjusted by attaching a condenser at the head of the respective column in which the respective vapour $B_1$ or $B_2$ is at least partially condensed and is supplied again to the respective RD. Generally and in the context of this invention, a return ratio is to be understood as meaning the ratio of the mass flow (kg/h) recycled to the respective column in liquid form (return) to the mass flow (kg/h) discharged from the respective column in liquid form (distillate) or gaseous form (vapours).

In the embodiment in which a return flow is established for the reaction column, the NaOH or KOH used in steps (a) or (b) are also mixed with the return stream and the resulting mixture then fed to the respective step.

$B_1$ and $B_2$ are at least partially mixed in accordance with the invention to give Bra and from this ROH is at least partially separated off and thus recovered by distillation of $B_M$. The at least partial distillative separation of ROH from $B_M$ is preferably carried out in a rectification column, which preferably has a return flow.

In the process according to the invention, the rectification column used can be any distillation column known to those skilled in the art. Distillation columns typically used have internals. Suitable internals are, for example, trays, unstructured packings or structured packings. Trays used are typically bubble cap trays, sieve trays, valve trays, tunnel cap trays or slit trays. Unstructured packings are generally random packings. The packings used are typically Raschig rings, Pall rings, Berl saddles or Intalox® saddles. Structured packings are, for example, sold under the trade name Mellapack® by Sulzer. In addition to the internals mentioned, suitable internals are known to those skilled in the art and may also be used.

Preferred internals have a low specific pressure loss per theoretical plate. Structured packings and random packings have, for example, a significantly lower pressure loss per theoretical plate than trays. This has the advantage that the pressure loss in the distillation column remains as low as possible and therefore the mechanical power of the compressor and the temperature of the methanol/water mixture to be evaporated remains low.

If structured packings or unstructured packings are present in the column, these can be divided or can be a continuous packing. Typically however, at least two packings are provided, one packing above the feed point of the ROH water mixture $B_M$ and one packing below the feed point of the ROH/water mixture $B_M$. If an unstructured packing is used, for example a random packing, the packings typically rest on a suitable sieve tray or mesh tray.

The at least partial mixing of $B_1$ and $B_2$ to give $B_M$ is effected particularly in that $B_1$ and $B_2$ are led from the reaction space of the respective RD and are mixed at least partially in a rectification column to give $B_M$ or are at least partially mixed beforehand to give $B_M$ and $B_M$ is then fed to the rectification column. More preferably, they are at least partially mixed beforehand to give $B_M$ and $B_M$ is then fed to the rectification column.

Preferably, $B_M$ is separated into water and alcohol ROH in the rectification column, wherein the alcohol ROH obtained by the separation stage is preferably fed to the reaction column as recycled alcohol ROH.

The reaction column in the first preferred embodiment of the process according to the invention can be operated using either recycled alcohol ROH from the rectification column or using fresh alcohol ROH. Preferably, both recycled alcohol ROH and fresh alcohol ROH is fed to the reaction column. Optionally, the fresh alcohol can be fed to the reaction column at a separate feed point or can be fed to the reaction column together with the recycled alcohol.

The alcohol ROH, in particular the fresh alcohol ROH, recycled alcohol ROH, or a mixture of both, but preferably recycled alcohol ROH, in the first preferred embodiment of the process according to the invention, is preferably fed in vaporous form to the reaction column at least twenty trays below the feed point of the alkali metal hydroxide solution. The preferably recycled alcohol is preferably metered in 1 to 10 trays, particularly preferably 1 to 6 trays above the bottoms or directly into the bottom of the reaction column. The preferably recycled alcohol ROH is very particularly preferably metered in below the lowest tray of the respective reaction column.

The rectification column preferably has a return flow, more preferably a condenser. The return ratio is preferably 0.5 to 2, more preferably 0.8 bis 1.6.

In a preferred embodiment of the first embodiment of the process according to the invention, fresh alcohol ROH is fed to the upper section of the rectification column, particularly together with the return flow of the rectification column. The alcohol ROH can be fed either to the rectifying section of the rectification column or directly at the head. The optimal feed point depends on the water content of the alcohol ROH used and also on the desired residual water content in the distillate. The higher the portion of water in the alcohol used and the higher the purity requirements in the distillate, the more advantageous is a feed a number of theoretical trays below the top of the rectification column. Up to 20 theoretical trays below the top of the rectification column, in particular 1 to 5 theoretical trays, are preferred.

This embodiment of the first preferred embodiment of the process according to the invention is particularly suitable to remove excess water from the alcohol ROH before the alcohol is recycled to the reaction column.

If, in the first preferred embodiment of the process according to the invention, the rectification column has at least one condenser, the fresh alcohol is particularly preferably added to the condenser or in to a condensate reservoir of the rectification column, the fresh alcohol particularly preferably being added to the condenser of the rectification column.

In the first preferred embodiment of the process according to the invention, the fresh alcohol is particularly added to the return flow of the respective reaction column, and this can be carried out in the condenser and in the condensate reservoir of the respective reaction column.

In a further preferred embodiment of the first preferred embodiment of the process according to the invention, one of the two reaction columns is configured as side column to the other. In this case, the one of the two columns which is not configured as side column has in particular a rectifying section, which in turn comprises preferably up to 5 theoretical trays, more preferably 1 to 4 theoretical trays, most preferably 2 to 3 theoretical trays. The rectifying section offers the advantage of preventing carry over of liquid into the mixed vapours.

Figure 1:
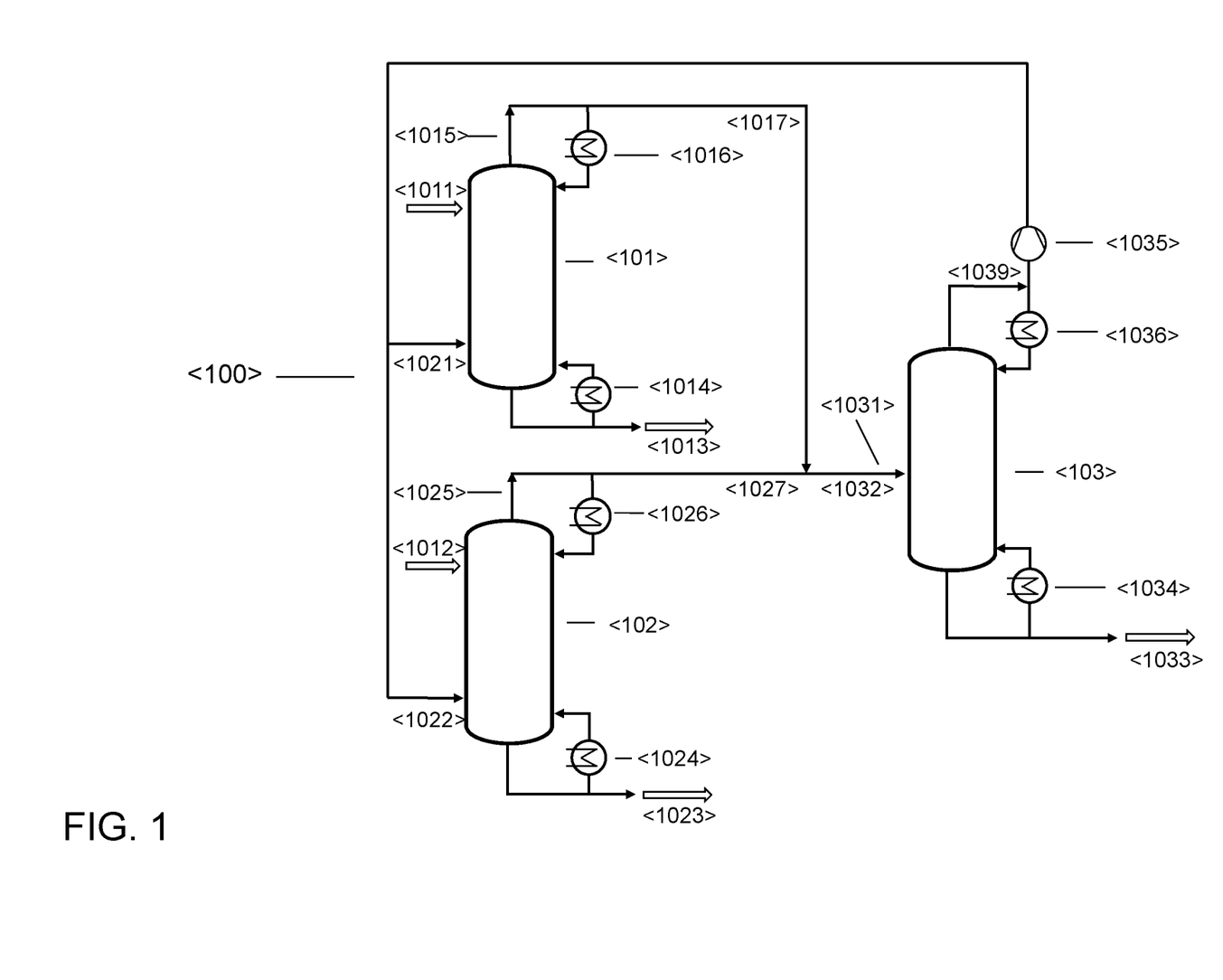
FIG. 1 shows one embodiment of the process according to the invention in which NaOH <1011> and KOH <1012> are each reacted in two separate reaction columns <101>, <102> with methanol <1021> and <1022> to give the respective methoxide <1013> and <1023>. The resulting vapours <1015> and <1025> are fed as mixture <1031> to a water/methanol column <103>, in which methanol <1039> is recovered by distillation.

FIG. 1 shows an embodiment <100> according to the first preferred embodiment of the process according to the invention. It comprises two reaction columns <101> and <102>. An aqueous NaOH solution <1011> is added to the upper fifth of the reaction column <101> and an aqueous KOH solution <1012> is added to the upper fifth of the reaction column <102>. Alternatively, a methanolic NaOH solution and a methanolic KOH solution can be added. Above the bottom of the reaction columns, methanol is added (<1021> in reaction column <101> and <1022> in reaction column <102>). At the bottom of reaction column <101>, the product sodium methoxide <1013> is obtained. At the bottom of reaction column <102>, the product potassium methoxide <1023> is obtained. With evaporator <1014> or <1024> at the bottom of the respective column, the concentration of the respective alkali metal methoxide solution is adjusted to the desired value. At the head of the two reaction columns <101> and <102>, a vapour $B_1$ <1015> and a vapour $B_2$ <1025> is withdrawn. At the top of the two reaction columns <101> and <102>, a portion of the vapour stream is condensed in condenser <1016> or <1026> and liquid is returned to the head of reaction column <101> or <102> as return flow. The portion of vapour $B_1$ <1015>, which is not returned to column <101> as return flow, is thus passed through pipeline <1017>. The portion of vapour $B_2$ <1025>, which is not returned to column <102> as return flow, is thus passed through pipeline <1027>. The respective portions of the two vapours $B_1$ <1015> and $B_2$ <1025> mix in pipeline <1032> to give the mixed vapour $B_M$ <1031>. This is supplied to the rectification column <103>. Distillation of methanol <1039> takes place therein which is discharged at the head. A condenser <1036> is also located at the head of the rectification column <103>, by means of which a portion of the methanol is condensed from <1039> and liquid is returned to the head of the rectification column <103>. The remaining methanol is then fed back again to the reaction columns (<1021> to reaction column <101> and <1022> to reaction column <102>) via the compressor <1035>. It can also be mixed here with fresh methanol. The compressor <1035> can alternatively also be installed in the pipeline <1032>, in which the mixed vapour $B_M$ <1031> is passed to the rectification column <103>. At the bottom of column <103>, water <1033> is withdrawn. The column <103> is heated with the aid of the evaporator <1034>.

Figure 2:
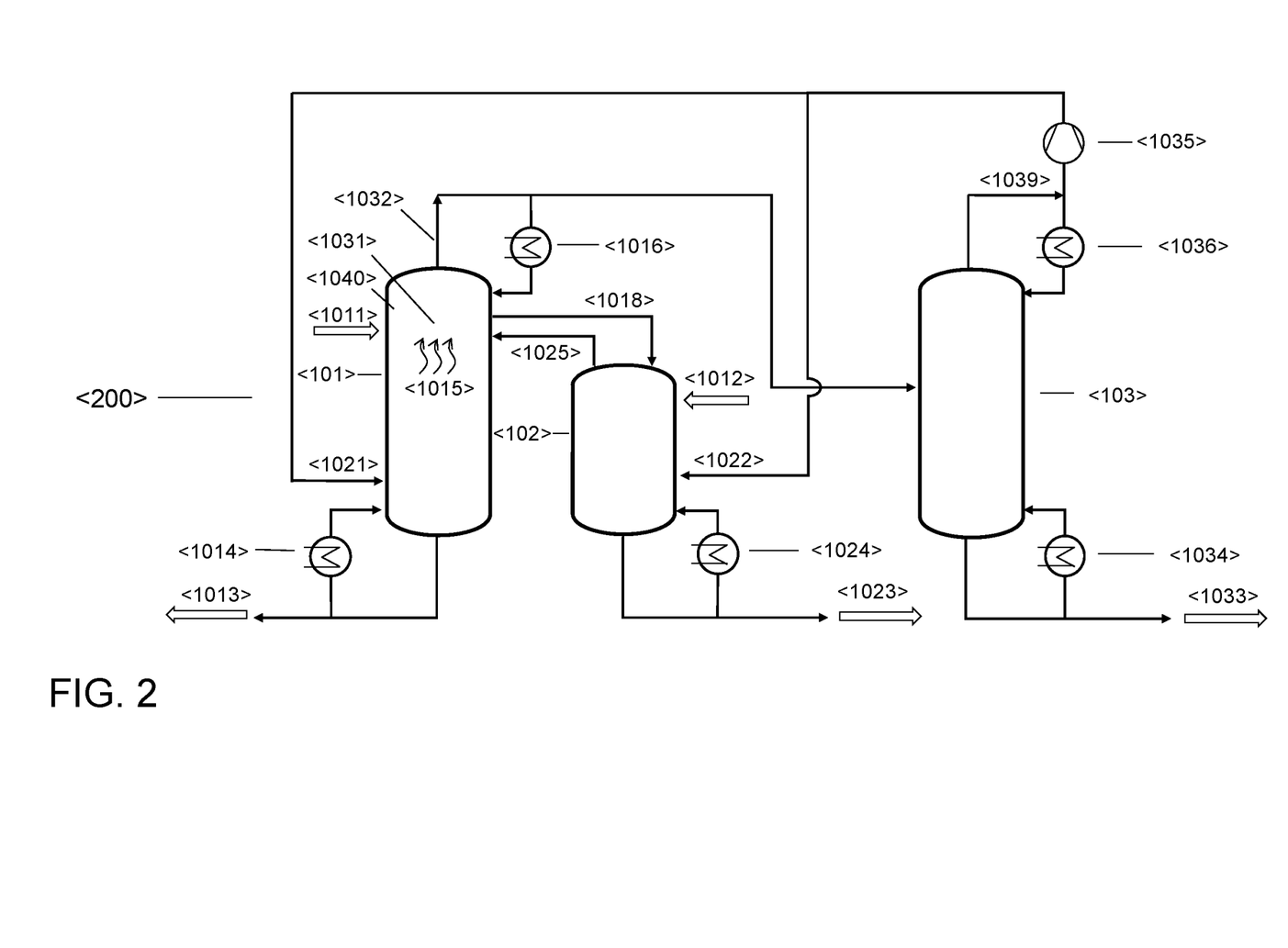
FIG. 2 shows one embodiment of the process according to the invention in which NaOH <1011> and KOH <1012> are each reacted in two separate reaction columns <101>, <102> with methanol <1021> and <1022> to give the respective methoxide <1013> and <1023>. The KOH column <102> is in this case configured as side column to the NaOH column <101>. The resulting vapours <1015> and <1025> are mixed in the upper region of column <101>. The mixture <1031> obtained at the head of column <101> is fed to a water/methanol column <103> in which methanol <1039> is recovered by distillation.

FIG. 2 shows a further embodiment <200> according to the first preferred embodiment of the process according to the invention. This corresponds to the embodiment shown in FIG. 1 and differs therefrom in that the reaction column for potassium methoxide <102> is configured as side column to the reaction column for sodium methoxide <101>. An aqueous NaOH solution <1011> is added to the upper quarter of the reaction column <101> and an aqueous KOH solution <1012> is added to the upper fifth of the side column <102>. The vapour $B_2$ <1025> is therefore already mixed in column <101> with the vapour $B_1$ <1015> (symbolized by curved arrows). As a result, a mixed vapour $B_M$ <1031> is ultimately obtained, which is at least partially withdrawn at the head of the column <101> via the pipeline <1032>. The column <101> can optionally comprise a rectifying section <1040> having preferably up to 5 theoretical stages in order to avoid carry over of liquid into the mixed vapour $B_M$ <1031>. Furthermore, a return flow can be passed into the column <101> via the condenser <1016>. A liquid stream from column <101> can be wholly or partially passed into column <102> via pipeline <1018>. The meaning of the symbols <103>, <1013>, <1014>, <1021>, <1022>, <1023>, <1024>, <1033>, <1034>, <1035>, <1036> and <1039> in FIG. 2 are as specified for FIG. 1.

Second Preferred Embodiment: a and (b) in One Reaction Column

In a second preferred embodiment of the process according to the invention, the spatial separation of the two reactions (a) and (b) is accomplished by carrying out the reaction according to (a) and the reaction according to (b) in the same reaction column in which they are separated from each other by at least one dividing wall. Such reaction columns are referred to below as dividing wall reaction columns. "Dividing wall reaction columns" are abbreviated below as "DRC". The at least one DRC used in the second preferred embodiment of the process according to the invention preferably has a rectifying section above the dividing wall.

DRCs are in principle obtained from conventional reaction columns into which a dividing wall is inserted, thus forming two separate reaction spaces.

Such dividing wall columns are familiar to those skilled in the art and are described for example in U.S. Pat. No. 2,295,256, EP 0 122 367 A2, EP 0 126 288 A2, WO 2010/097318 A1 and I. Dejanović, Lj. Matijašević, . Olujić, *Chemical Engineering and Processing* 2010, 49, 559-580. In the dividing wall columns suitable for the process according to the invention the dividing walls preferably extend to the column floor and, in particular, preferably span at least a quarter, more preferably at least a third, yet more preferably at least half, yet more preferably at least two thirds, yet still more preferably at least three quarters, of the column by height. They divide the columns into at least two reaction spaces in which spatially separate reactions may be carried out. The reaction spaces provided by the at least one dividing wall may be of identical or different sizes.

The reaction column which is used in the second preferred embodiment of the process according to the invention comprises at least one dividing wall, preferably one dividing wall or two dividing walls. In particular, DRCs also have a return flow.

In the second preferred embodiment of the process according to the invention, KOH and NaOH are in particular each fed to the upper half, preferably to the upper third, more preferably to the upper quarter, of the region of the reaction column spanned by the dividing wall. This ensures that the respective alkali metal hydroxide is only added to the reaction space in which it is intended to react and thus cross-contamination is avoided. At the same time, addition close to the upper edge (but below the upper edge) ensures the longest possible reaction time of the respective alkali metal hydroxide with ROH.

DRCs have the advantage that they are space-saving and the two vapours $B_1$ and $B_2$ mix at least partially above the dividing wall to give $B_M$.

In the second preferred embodiment of the process according to the invention, particularly the at least partial distillative separation of ROH from $B_M$ is then carried out in a rectification column different from the DRC. This rectification column preferably has a return flow, as is specified for the rectification column according to the first preferred embodiment.

Alternatively, the DRC in this second preferred embodiment of the process according to the invention in particular has rectifying section in which the rectification column is configured as side column to the DRC.

In a further alternative preferred embodiment according to the second preferred embodiment of the process according to the invention, the reaction according to (a), the reaction according to (b) and the distillative separation of ROH from $B_M$ are carried out in the same reaction column in which they are separated from one other by two dividing walls.

Three spaces separated from one another are formed by the two dividing walls, of which one is used for step (a), one for step (b) and one for the distillative separation of ROH from $B_M$.

As a result, $B_M$ can be separated at least partially into water and ROH by distillation in the same DRC by creating a further space by means of a second dividing wall and ROH can thus be recovered. The reaction according to (a), the reaction according to (b) and the at least partial distillative separation of ROH from $B_M$ are thus carried out in the same reaction column in which they are separated from one another by two dividing walls (which create three segregated regions).

Figure 3:
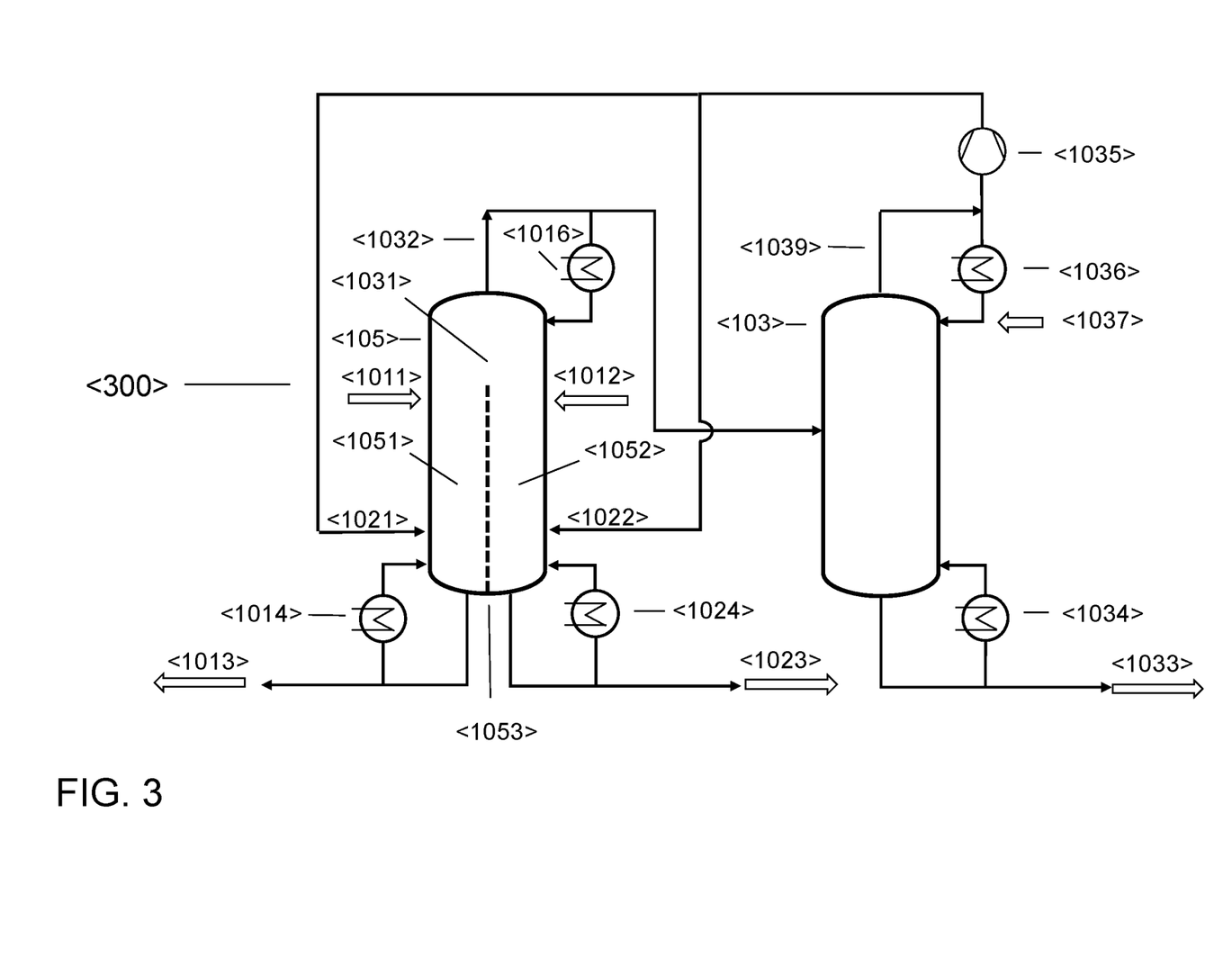
FIG. 3 shows one embodiment of the process according to the invention in which NaOH <1011> and KOH <1012> are reacted with methanol <1021> and <1022> in a single reaction column <105> with downward extending dividing wall <1053> to give the respective methoxide <1013> and <1023>. NaOH <1011> and KOH <1012> is added to reaction column <105> on different sides of the dividing wall <1053> below the upper edge. The resulting vapours are fed as mixture <1031> to a water/methanol column <103>, in which methanol <1039> is recovered by distillation.

FIG. 3 shows an embodiment <300> according to the second preferred embodiment of the process according to the invention. It comprises a reaction column <105>, which comprises a vertical dividing wall <1053> extending to the floor of the column, such that two reaction spaces <1051> and <1052> are formed in the column.

An aqueous NaOH solution <1011> is added to the reaction space <1051>. An aqueous KOH solution <1012> is added to the reaction space <1052>. Alternatively, a methanolic NaOH solution and a methanolic KOH solution can each be added. The addition point is located beneath the height which defines the upper end of the dividing wall <1053> since it is avoided that the respective alkali metal hydroxide flows into the wrong reaction space. Above the bottom of the reaction columns, methanol is added (<1021> in reaction space <1051> and <1022> in reaction space <1052>). At the bottom of the reaction column <105>, the product sodium methoxide <1013> and the product potassium methoxide <1023> are obtained. With evaporators <1014> and <1024> at the bottom of the respective column, the concentration of the two alkoxide solutions are adjusted to the desired value. The mixed vapour $B_M$ <1031> is obtained in reaction column <105> from the mixture of the two vapours and is at least partially withdrawn via pipeline <1032> at the head of the column <101>. A condenser <1016> is located at the top of the reaction column <105> via which a return flow can be passed into the column <105>. The vapour mixture $B_M$ <1031> is fed at least partially to the rectification column <103> via the pipeline <1032>. The distillative separation of methanol <1039> takes place therein which is discharged at the head. A condenser <1036> is also located at the head of the rectification column <103>, by means of which a portion of the methanol is condensed <1039> and is returned to the head of the column <103>. Fresh methanol <1037> can be supplied to the condenser <1036>. Fresh methanol <1037> can also be added in the embodiments of the process according to the invention which are shown in FIGS. 1 and 2. The remaining methanol is then fed again to the reaction column <105> via the compressor <1035>. It can also be mixed here with fresh methanol <1037>. The compressor <1035> can also alternatively be installed in pipeline <1032>, in which at least a portion of the vapour mixture $B_M$ <1031> is passed into the rectification column <103>, more preferably in the section of the pipeline <1032> through which flows at least a portion of the vapour mixture $B_M$ <1031> after passing the branching to the condenser <1016>.

At the bottom of column <103>, water <1033> is withdrawn. The column <103> is heated with the aid of the evaporator <1034>.

Figure 4:
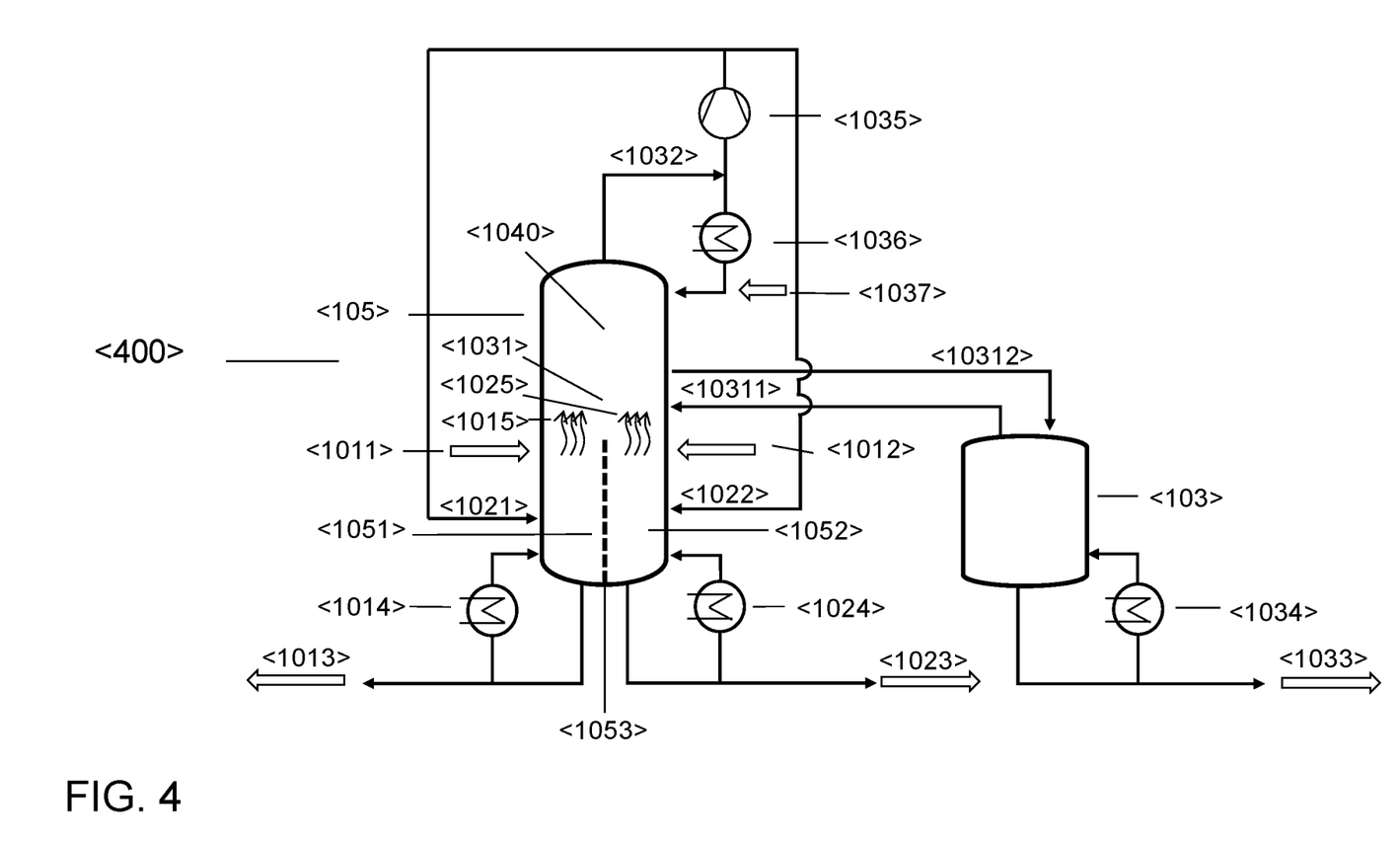
FIG. 4 shows one embodiment of the process according to the invention in which NaOH <1011> and KOH <1012> are reacted with methanol <1021> and <1022> in a single reaction column <105> with downward extending dividing wall <1053> and rectifying section <1040> to give the respective methoxide <1013> and <1023>. The distillative recovery of methanol from the vapours <1015>, <1025> from reaction spaces <1051> and <1052> on both sides of the dividing wall <1053> is effected in rectifying section <1040> of reaction column <105> and the stripping section provided as side column <103>.

FIG. 4 shows a further embodiment <400> according to the second preferred embodiment of the process according to the invention. This corresponds to the embodiment shown in FIG. 3 and differs therefrom in that the stripping section of the distillation column <103> is provided as side column of the dividing wall column <105> and the rectifying section <1040> is integrated into the column <105>. The vapour $B_2$ <1025> is therefore already mixed in column <105> with the vapour $B_1$ <1015> and the vapour <10311> of column <103>. Methanol is recovered from the vapours of the reaction sections <1051> and <1052> by distillation in the rectifying section of <105> and water is separated off in the side column <103>. The columns <105> and <103> are linked via the liquid stream <10312> and the vapour stream <10311>. The methanol obtained is then partially withdrawn via pipeline <1032> of column <105> and reused in the reaction sections via <1021> and <1022>. The other portion is used for the return flow, which is recycled via the condenser <1036> to the column <105>.

The meaning of the symbols <1011>, <1012>, <1013>, <1014>, <1023>, <1024>, <1031>, <1033>, <1034>, <1035>, <1037>, <1051>, <1052> and <1,053> in FIG. 4 are as specified for FIG. 3.

Figure 5:
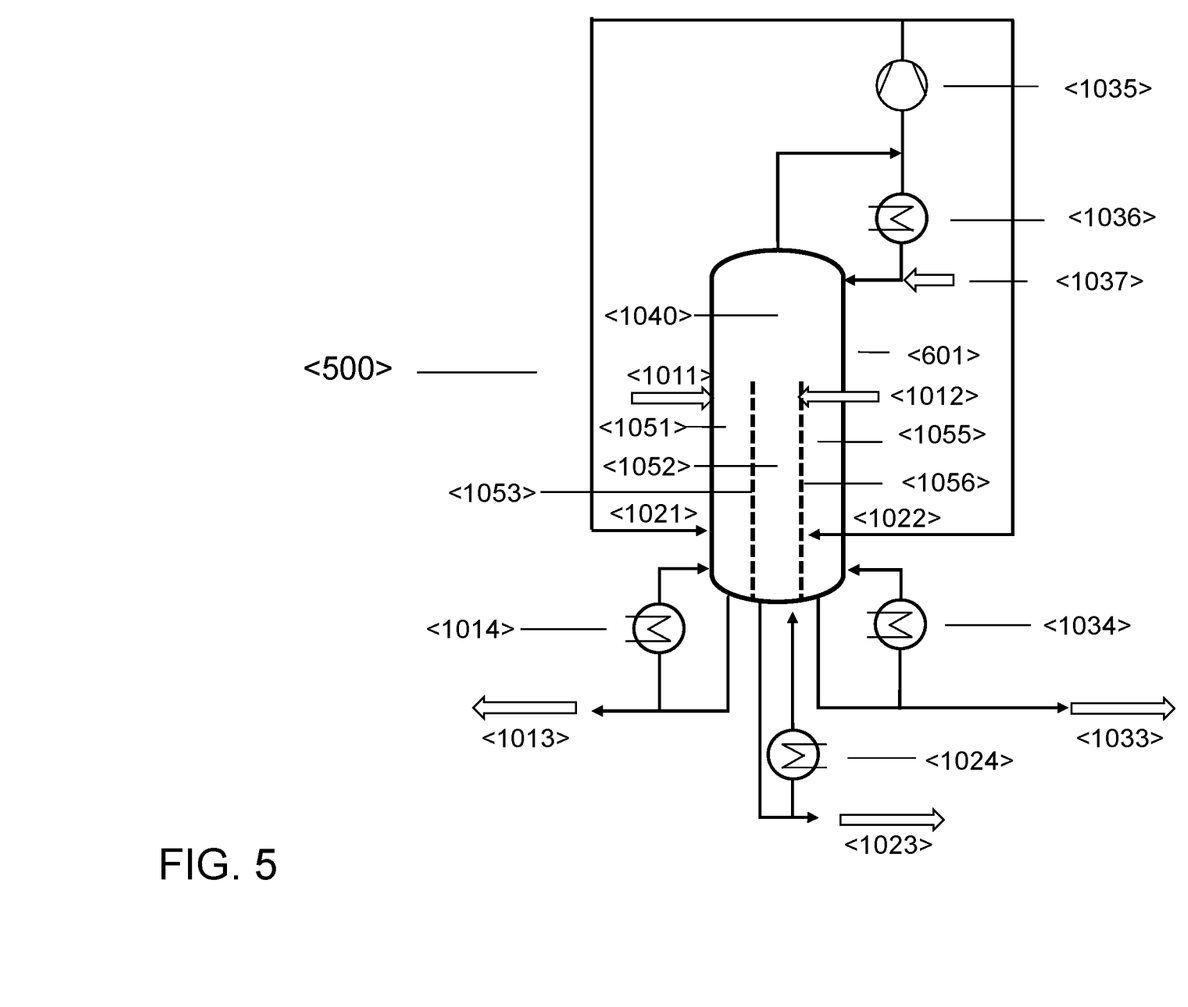
FIG. 5 shows one embodiment of the process according to the invention in which NaOH <1011> and KOH <1012> are reacted with methanol <1021> and <1022> in a single reaction column <601> with two downward extending dividing walls <1053>, <1056> and rectifying section <1040> to give the respective methoxide <1013> and <1023>. The resulting vapours are separated by distillation in rectifying section <1040> and in stripping section <1055> of reaction column <105>.

FIG. 5 shows a further embodiment <500> according to the second preferred embodiment of the process according to the invention. This corresponds to the embodiments shown in FIGS. 3 and 4 and is differentiated by a reaction column <601> having two dividing walls <1053> and <1058>. By constructing two dividing walls <1053> and <1056>, the lower section of the column is divided into three separated spaces: the two reaction spaces <1051>, <1052> and the stripping section <1055>. In the reaction spaces <1051> and <1052>, the reaction of the aqueous NaOH solution <1011> and the aqueous KOH solution <1012> proceeds in each case with methanol (<1021> in the reaction space <1051> and <1022> in the reaction space <1052>) to give sodium methoxide or potassium methoxide, while the separation of methanol and water proceeds in the stripping section <1055>.

The meaning of the symbols <1011>, <1012>, <1013>, <1014>, <1021>, <1022>, <1023>, <1024>, <1033>, <1034>, <1035>, <1036>, <1037> and <1040> in FIG. 5 are as specified for FIG. 3.

3. Third Preferred Embodiment: Distillation and One of the Steps (a), (b) in One Reaction Column the Other Step in the Side Column In a third preferred embodiment of the process according to the invention, said process is carried out in one DRC and a side column, wherein the DRC preferably comprises a rectifying section. The DRC comprises a dividing wall whereby two regions segregated by the dividing wall are formed in the DRC.

In this embodiment, one of the two steps (a) or (b) of the process according to the invention takes place in one of the regions of the DRC segregated by the dividing wall, and the other of the two steps in the side column. The at least partial distillative separation of ROH from $B_M$ takes place in the region of the DRC segregated by the dividing wall in which neither of the steps (a), (b) of the process according to the invention is carried out, and in preferred cases in which the DRC comprises this, in the rectifying section.

When using a DRC this embodiment enables a better spatial separation of steps (a) and (b) since one of them is carried out in the DRC and the other in the side column.

EXAMPLES

Example 1 (Non-Inventive): Use of Only One Reaction Column, Without Washing Step The reaction column is initially operated continuously with a stream of aqueous NaOH from a first alkaline tank (Tank 1) and methanol in countercurrent. The sodium methoxide produced in this case (dissolved in methanol) leaves the reaction column at the bottom and comprises only very small amounts of NaOH and water (ca. 1000 ppm). A methanol-water mixture exits the reaction column in vapour form at the top and is continuously fed to the downstream rectification column. Here, the methanol-water mixture is separated and a virtually anhydrous methanol stream is obtained at the top and also a virtually methanol-free water stream at the bottom of the column. The recovered methanol is recycled to the column in vapour form and introduced there above the bottoms.

For the subsequent production of potassium methoxide, the plant is shut down and the bottoms of the reaction column emptied in order to remove the sodium methoxide solution contained therein. This procedure takes several hours in which no production can take place. Further rinsing of the column is not carried out for reasons of time. The plant is then restarted with a feed of aqueous KOH to the reaction column from a second alkaline tank (Tank 2). The potassium methoxide solution withdrawn at the bottom of the reaction column also now comprises, in addition to the residue of unreacted KOH and water, the residues of NaOH and sodium methoxide from the column internals. Because of this, the potassium methoxide solution initially has very high contamination and must therefore be discarded. By dilution, the contamination only reaches an acceptable value (<5000 ppm) after some time. At this time point, a marketable product is produced but with distinctly worse quality than prior to the product changeover (<<1000 ppm). A subsequent, renewed change to the production of sodium methoxide is associated with the same steps.

Example 2 (Non-Inventive): Use of Only One Reaction Column, with Washing Step

The reaction column is initially operated continuously with a stream of aqueous NaOH from a first alkaline tank (Tank 1) and methanol in countercurrent. The sodium methoxide produced in this case (dissolved in methanol) leaves the reaction column at the bottom and comprises only very small amounts of NaOH and water (ca. 1000 ppm). A methanol-water mixture exits the reaction column in vapour form at the top and is continuously fed to the downstream rectification column. Here, the methanol-water mixture is separated and a virtually anhydrous methanol stream is obtained at the top and also a virtually methanol-free water stream at the bottom of the column. The recovered methanol is recycled to the column in vapour form and introduced there above the bottoms.

For the subsequent production of potassium methoxide, the plant is shut down and the bottoms of the reaction column emptied in order to remove the sodium methoxide solution contained therein. This procedure takes several hours in which no production can take place. Subsequently, the plant is thoroughly cleaned in order to avoid contamination of the potassium methoxide by residues in the reaction column. For this purpose, the reaction column is rinsed with steam several times in succession and emptied. This procedure also takes several hours in which ria production can take place. Also in this case, large amounts of steam are consumed. The plant is then restarted with a feed of aqueous KOH to the reaction column from a second alkaline tank (Tank 2). The potassium methoxide solution withdrawn from the bottoms of the reaction column comprises only very small amounts of KOH and water and also very low residues of NaOH and sodium methoxide. This solution can be marketed directly due to the rinsing step, but still has minor impurities of NaOH and sodium methoxide.

Example 3 (Inventive), Corresponds to FIG. 1

Sodium methoxide and potassium methoxide are produced in two simultaneously and continuously operated reaction columns. The first reaction column <101> is operated continuously with a stream of aqueous NaOH <1011> from a first alkaline tank (Tank 1) and methanol <1021> in countercurrent. The sodium methoxide produced in this case (dissolved in methanol) leaves the reaction column at the bottom <1013> and comprises only very small amounts of NaOH and water (ca. 1000 ppm). A methanol-water mixture <1015> exits the reaction column in vapour form at the top. The second reaction column <102> is operated continuously with a stream of aqueous KOH <1012> from a second alkaline tank (Tank 2) and methanol <1022> in countercurrent. The potassium methoxide produced in this case (dissolved in methanol) leaves the reaction column at the bottom <1023> and comprises only very small amounts of KOH and water (Ca. 1000 ppm). A methanol-water mixture <1025> exits the reaction column in vapour form at the top. Both methanol-water mixtures at the top of the reaction columns are mixed and together fed continuously as mixture <1031> to the downstream rectification column <103>. Here, the methanol-water mixture <1031> is separated and a virtually anhydrous methanol stream <1039> is obtained at the top and also a virtually methanol-free water stream <1033> at the bottom of the column. The recovered methanol is recycled to both reaction columns in vapour form and introduced there in each case above the bottoms.

Example 4 (Inventive): Corresponds to FIG. 3

The reaction column <105> has a downward extending dividing wall <1053> placed centrally. Two spatially separated reaction spaces <1051> and <1052> are formed in this case in which two reactions can proceed simultaneously. Above the dividing wall are only three valve trays. On the first side of the dividing wall, a stream of aqueous NaOH <1011> is fed continuously from a first alkaline tank (Tank 1) and methanol <1021> in countercurrent. The sodium methoxide produced in this case (dissolved in methanol) leaves the reaction column at the bottom <1013> and comprises only very small amounts of NaOH and water (ca. 1000 ppm). On the second side of the dividing wall, a stream of aqueous KOH <1012> is fed continuously from a second alkaline tank (Tank 2) and methanol <1022> in countercurrent. The potassium methoxide produced in this case (dissolved in methanol) leaves the reaction column at the bottom <1023> and comprises only very small amounts of KOH and water (ca. 1000 ppm). In each case a vaporous methanol-water mixture exits at the upper end of the dividing wall on both sides of the dividing wall. These mix above the dividing wall. The resulting methanol-water mixture <1031> exits the reaction column in vapour form at the top and is continuously fed to the downstream rectification column <103>. Here, the methanol-water mixture is separated and a virtually anhydrous methanol stream <1039> is obtained at the top and also a virtually methanol-free water stream <1033> at the bottom of the column. The recovered methanol is recycled in vapour form to the reaction column, divided and introduced on both sides of the dividing wall above both bottoms.

Result:

The use of only one reaction column as in Example 1 and 2 entails disadvantages, namely cross-contamination of sodium methoxide in potassium methoxide and vice versa, which could only be avoided by laborious cleaning. In contrast, the process according to the invention, as shown in Examples 3 and 4, allows a pure production of the respective methoxides at high purity without production downtime.

The invention claimed is:

1. A process for producing sodium alkoxide of the formula RONa and potassium alkoxide of the formula ROK, the process comprising;
   (a) reacting ROH with NaOH in countercurrent, wherein the RONa and a vapour $B_1$ comprising water and ROH are obtained,
   (b) reacting ROH with KOH in countercurrent, wherein the ROK and a vapour $B_2$ comprising water and ROH are obtained,
   wherein R is a $C_1$-$C_6$-hydrocarbon radical,
   wherein the reactions according to (a) and (b) proceed simultaneously and are spatially separated,
   wherein the vapour $B_1$ and the vapour $B_2$ are at least partially mixed to give g mixed vapour BM comprising ROH and water, and
   wherein the ROH is at least partially separated off from $B_M$ by distillation.

2. The process according to claim 1, wherein the ROH separated off from $B_M$ is used again in the reaction (a) and/or the reaction (b).

3. The process according to claim 1, wherein ROH is selected from the group consisting of methanol, ethanol, n-propanol, isopropanol, n-butanol, sec-butanol, isobutanol, tert-butanol, and an isomer of pentanol.

4. The process according to claim 1, wherein the NaOH in the reaction according to (a) and/or the KOH in the reaction according to (b) is added in at least one solvent selected from the group consisting of water, ROH, and a mixture thereof.

5. The process according to claim 1, wherein the reaction according to (a) is carried out in a first reaction column and the reaction according to (b) is carried out in a second reaction column different from the first reaction column.

6. The process according to claim 5, wherein the KOH and the NaOH are each fed to an upper half of the respective reaction column of the first reaction column and the second reaction column.

7. The process according to claim 5, wherein the first reaction column and/or the second reaction column has a return flow.

8. The process according to any claim 5, wherein the at least partial distillative separation of the ROH from $B_M$ is carried out in a rectification column.

9. The process according to claim 5, wherein one of the first reaction column and the second reaction column is configured as a side column to the other.

10. The process according to claim 1, wherein the reaction according to (a) and the reaction according to (b) are carried out in the same reaction column in which they are separated from each other by at least one dividing wall.

11. The process according to claim 10, wherein the KOH and the NaOH are each fed to an upper half of a region of the reaction column spanning the at least one dividing wall.

12. The process according to claim 10, wherein the at least partial distillative separation of the ROH from $B_M$ is carried out in a rectification column different from the reaction column.

13. The process according to claim 12, wherein the reaction column has a rectifying section and the rectification column is configured as a side column to the reaction column.

14. The process according to claim 10, wherein the reaction according to (a), the reaction according to (b), and the at least partial distillative separation of the ROH from $B_M$ are carried out in the same reaction column in which they are separated from one other by two dividing walls.

15. The process according to claim 1, wherein said process is carried out in a reaction column comprising a dividing wall, and a side column to the reaction column,
wherein one of (a) and (b) is carried out in a region of the reaction column segregated by the dividing wall, and the other of (a) and (b) is carried out in the side column, and the at least partial distillative separation of the ROH from $B_M$ takes place in a region of the reaction column segregated by the dividing wall in which neither of (a) nor (b) is carried out.

16. The process according to claim 1, wherein said process is carried out continuously.

* * * * *